United States Patent [19]

Muramatsu et al.

[11] Patent Number: 5,334,303
[45] Date of Patent: Aug. 2, 1994

[54] ELECTROCHEMICAL MEASUREMENT SYSTEM

[75] Inventors: Hiroshi Muramatsu; Xuanjing Ye, both of Tokyo, Japan

[73] Assignee: Seiko Instruments Inc., Japan

[21] Appl. No.: 851,752

[22] Filed: Mar. 16, 1992

[30] Foreign Application Priority Data

Mar. 22, 1991 [JP] Japan .................. 3-058998
Apr. 9, 1991 [JP] Japan .................. 3-076558

[51] Int. Cl.⁵ .................. G01N 27/26; H01L 41/00
[52] U.S. Cl. .................. 204/412; 204/153.1; 204/180.2; 204/400; 204/404; 204/434; 310/311; 310/312; 310/313 R; 310/321; 310/363; 310/364; 422/98
[58] Field of Search .................. 204/153.1, 400, 412, 204/434, 404; 310/311, 312, 313 R, 321, 323, 324, 363, 364; 73/61 R, 61.1 R, 61.2; 435/4.7, 29, 32, 34, 817; 436/532–535, 806; 422/57, 98

[56] References Cited

U.S. PATENT DOCUMENTS

4,661,210  4/1987  Tenygl .................. 204/153.1
4,789,804  12/1988  Karube et al. .................. 310/311
4,831,324  5/1989  Asakura et al. .................. 204/404

FOREIGN PATENT DOCUMENTS

0215669  3/1987  European Pat. Off. .
0282332  9/1988  European Pat. Off. .

OTHER PUBLICATIONS

Patent Abstracts of Japan, vol. 12, No. 188 (P-711), Jun. 2, 1988.

*Primary Examiner*—T. Tung
*Attorney, Agent, or Firm*—Bruce L. Adams; Van C. Wilks

[57] ABSTRACT

A quartz crystal resonator is utilized to effect evaluation of the viscoelastic characteristic of a film deposited on an electrode by an electrochemical reaction. The quartz crystal resonator is connected to a resonator characteristic measurement unit comprised of an oscillating circuit, a frequency counter, and an amplitude level meter. An electrochemical measurement unit in the form of a potentiostat is connected to a working electrode which comprises one of the electrodes of the resonator, to a reference electrode and to a counter electrode. The frequency counter, the amplitude level meter and the potentiostat are connected to a CPU. The resonator, reference electrode and counter electrode are all immersed in an electrolyte solution in an electrochemical cell. In another embodiment, the system utilizes a quartz crystal resonator precoated with a macromolecule sensitive film for analyzing diffusion and viscosity variation in the film due to migration of electrochemically active substances relative to the film during the course of the electrochemical reaction.

17 Claims, 8 Drawing Sheets

ELECTROCHEMICAL MEASUREMENT SYSTEM

BACKGROUND OF THE INVENTION

The present invention relates to a system for measuring and analyzing electrochemical reactions associated with the field of chemistry, biology, physics, medicine, environmental engineering, energy science, electronics and their related fields.

In the chemical measurement technology utilizing a quartz crystal resonator as a sensing element, there has been known a conventional method of measuring a resonant frequency variation indicative of a surface mass deposition on an electrode of the resonator or indicative of a viscosity and density variation of a fluid in contact with the resonator electrode. This method is applied such that, for example, the resonant frequency variation of the quartz crystal resonator is monitored during the course of an electrochemical reaction so as to analyze the electrochemical reaction, such as, formation of an electrolytically polymerized film or the corrosion of an electrode. On the other hand, the inventors have proposed another method based on the fact that a resonant resistance variation is caused by a viscosity and density variation in a surrounding fluid or in a viscoelastic coating film disposed in contact with an electrode surface on the resonator.

In the conventional electrochemical measurement method, the frequency variation is monitored to analyze a film deposition on the electrode surface or an electrode corrosion during the course of a tested electrochemical reaction. The monitored variation is treated straightforwardly to reflect mass variation. The resonant frequency variation may generally accurately reflect the mass effect on the surface of the quartz crystal resonator; however, in the case where a viscoelastic film is formed on the resonator by a certain electrochemical reaction, it is practically difficult to accurately monitor a deposit mass of the viscoelastic film due to attenuation of the resonator vibration through the film. Therefore, it is important in the electrochemical measurement method utilizing the quartz crystal resonator to evaluate the nature of the film in order to analyze the film deposition reaction. From a different point of view, the conventional measurement method can only monitor a film deposition or growth process which occurs directly on the electrode surface during the course of the electrochemical reaction. Further, as mentioned before, only the resonant frequency variation is measured and the measurement results are treated straightforwardly to detect a mass deposit variation. In the case where a functional or sensitive film is provisionally applied over the electrode surface, the charge and discharge of active substances into and from the sensitive film is analyzed in terms of mass variation by the measurement of the resonant frequency variation alone according to the prior art, and hence it is difficult to discriminate actually between the viscous variation and the mass variation within the sensitive film. Accordingly, it would be certainly necessary to measure the resonant resistance variation which reflects both the viscosity variation and the mass variation which occur by the electrochemical reaction within the sensitive film over the quartz crystal resonator, as well as to measure the resonant frequency variation.

SUMMARY OF THE INVENTION

In order to solve the above noted problems, a first object of the invention is to realize accurate analysis of an electrochemical reaction such as a film deposition process directly on a working electrode. According to the first aspect of the invention, the electrochemical measurement system is comprised of a quartz crystal resonator, a characteristic measurement unit of the quartz crystal resonator and an electrochemical measurement unit. The characteristic measurement unit of the quartz crystal resonator includes an oscillating circuit for oscillating the resonator, a measurement circuit for measuring an oscillating frequency or resonant frequency of the resonator and another measurement circuit for measuring an amplitude level of the resonator indicative of a resonant resistance variation. The electrochemical measurement unit is comprised of a potentiogalvanostat connected to a working electrode exposed in an electrolyte solution and given in the form of an operating or driving electrode of the quartz crystal resonator, to a reference electrode and to a counter electrode. The electrochemical measurement unit further includes an electrode potential setting circuit and a cell current measurement circuit for measuring a cell current flowing through an electrochemical cell containing the working, counter and reference electrodes, or a cell current setting circuit and an electrode potential measurement circuit. By such construction, the system can monitor concurrently the cell current, the electrode potential, the resonant frequency variation and the resonant resistance variation during the course of the electrochemical reaction.

In the above described inventive system (FIG. 1), the oscillating circuit feeds at its output terminal an alternating current drive signal having an amplitude level VO to the quartz crystal resonator. After passing through the resonator, the alternating current drive signal is received by the oscillating circuit at its input terminal such that an amplitude level VQ of the received drive signal is a function of the resonant resistance RQ of the resonator and an input impedance RI of the oscillating circuit according to the relation RQ=(VO/VQ−1)RI. Stated otherwise, the resonant resistance RQ can be measured in terms of the amplitude level VQ.

The measured resonant frequency is generally dependent on both the mass deposit effect on the resonator surface and the viscous effect of the surrounding fluid. On the other hand, the resonant resistance is not varied by an elastic effect associated with the mass of a deposited film, but the resonant resistance generally reflects viscosity variation. In the particular case where a viscoelastic film is deposited, the resonant frequency significantly varies if the film has a strong elastic nature, and the resonant resistance varies in a relatively small range. On the other hand, if the viscoelastic film has a strong viscous nature, the resonant resistance variation may be greater due to the viscous nature than the resonant frequency variation.

Namely, the quartz crystal resonator is utilized such that both the resonant frequency variation and the resonant resistance variation are monitored concurrently with the measurement of the cell current and the electrode potential during the course of the electrochemical reaction so as to efficiently analyze the nature of a deposit film electrochemically grown on the electrode surface in the film deposition process.

A second object of the invention is to effectively analyze an electrochemical reaction conducted within a sensitive film preformed on an electrode. According to the second aspect of the invention, there is proposed an electrochemical measurement system utilizing a quartz crystal resonator coated with a sensitive macromolecule film and being constructed such as to measure variations of the quartz crystal resonator characteristics concurrently with electrochemical characteristics of the sensitive film, thereby enabling analysis of substance transformation or substance migration within the film caused by electrochemical reaction, in terms of electrode potential, cell current, resonant frequency variation, and resonant resistance variation.

When electrochemically active substances are subjected to an electrochemical reaction on a working electrode, a reduced form is converted into an oxidated form, or an oxidated form is converted into a reduced form. By such reaction, density profiles of the respective substances are varied in the vicinity of the electrode to thereby cause migration of the substances. In the cell structure where a drive electrode of the quartz crystal resonator is precoated with a sensitive macromolecule film to form the working electrode, there is caused migration of substances to and from the sensitive film due to density variation of the substances induced by the electrochemical reaction in the vicinity of the electrode. Such migration of the substances causes, within the film, mass shift or viscosity shift which can be detected in terms of variations in the characteristics of the quartz crystal resonator. Namely, behavior of the substances within the film can be well analyzed by monitoring variations in the characteristics of the quartz crystal resonator while concurrently monitoring electrochemical characteristics of the substances. Stated otherwise, the quartz crystal resonator precoated with the sensitive film is utilized to measure the resonant frequency variation and the resonant resistance variation during the course of the electrochemical reaction concurrently with the monitoring of the cell current and electrode potential so as to obtain detailed information concerning the nature of the reaction.

DETAILED DESCRIPTION OF THE PREFERRED EMBODIMENTS

Figure 1:
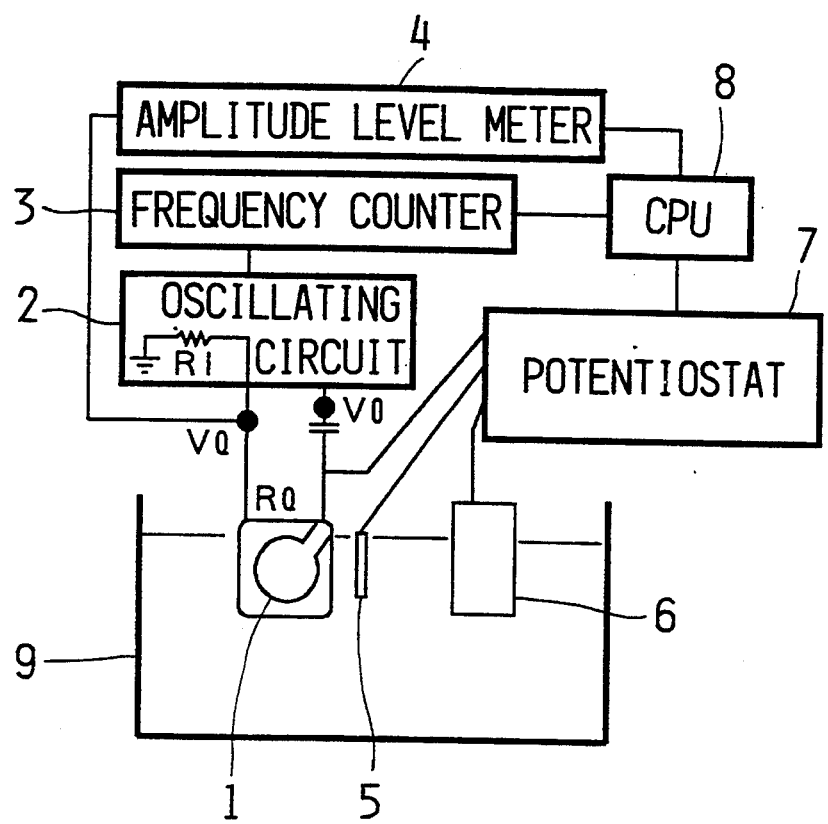
FIG. 1 is a schematic diagram of the electrochemical measurement system according to the present invention.

Hereinafter, embodiments of the invention will be described in conjunction with the drawings. FIG. 1 shows an overall construction of the inventive electrochemical measurement system. A quartz crystal resonator 1 is connected to a resonator characteristic measurement unit which includes an oscillating circuit 2, a frequency measurement circuit in the form of a frequency counter 3 and an amplitude level measurement circuit in the form of an amplitude level meter 4. On the other hand, an electrochemical measurement unit is comprised of a potentiostat 7 which is connected to a working electrode given in the form of one electrode of the quartz crystal resonator 1 as well as connected to a reference electrode 5 and a counter electrode 6. These electrodes are disposed within an electrolyte solution to constitute an electrochemical cell 9. Another electrode of the resonator 1 is electrically isolated from the electrolyte solution. The frequency counter 3, amplitude level meter 4 and potentiostat 7 are connected to a CPU 8 which analyzes measured results and which is provided with a record unit or display unit. The quartz crystal resonator 1, reference electrode 5 and counter electrode 6 are dipped into the electrolyte solution during the electrochemical measurement.

Hereinafter, the description is given for one application directed to the analysis of an electrolytic polymerization process of a pyrrole film. In this application, the counter electrode 6 is comprised of a platinum wire electrode, and the reference electrode 5 is comprised of an Ag/AgCl electrode. The electrolyte solution is comprised of a 20 mM phosphoric acid butter solution of pH 7 containing 0.2M pyrrole and 0.1M $KNO_3$. The quartz crystal resonator is comprised of an AT cut type crystal having a frequency of 9 MHz.

The inventive measurement system was operated to measure the amplitude VQ. The result of the measurement was compared to a value of the resonant resistance RQ which was separately measured by an external impedance analyzer. The comparison proved the linear relation between RQ and 1/VQ.

Figure 2:
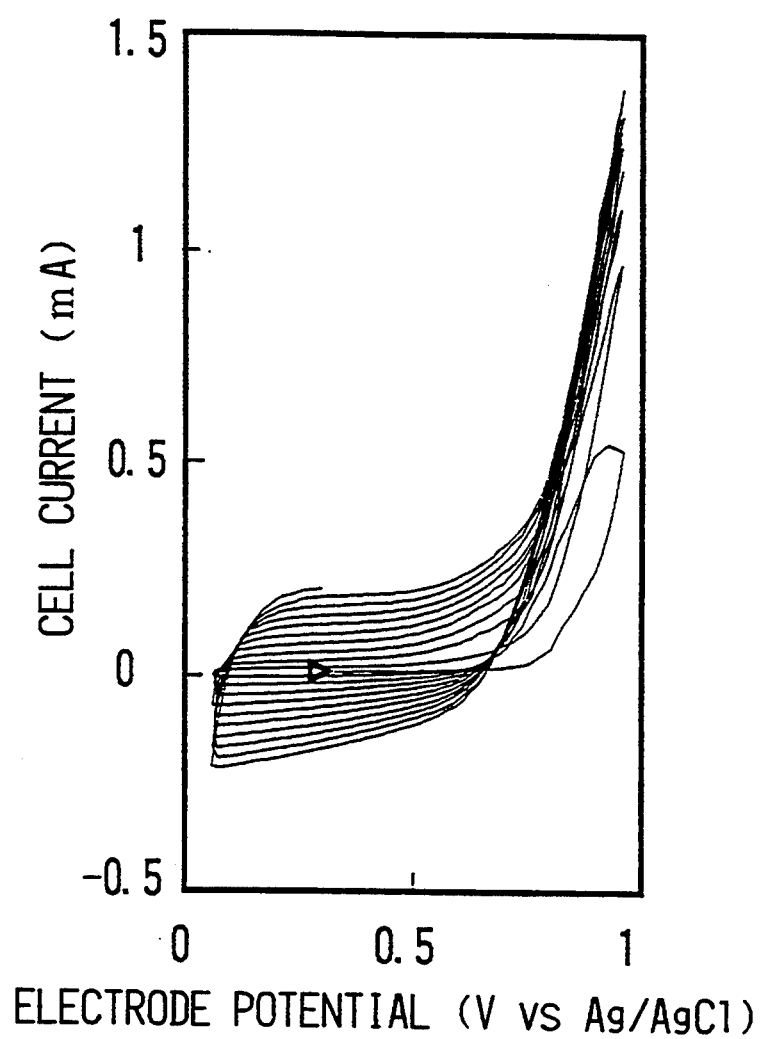
FIG. 2 is a graph showing an example of the current vs. potential curve measured by the inventive electrochemical measurement system during the course of the electrolytic polymerization reaction of polypyrrole.
Figure 3:
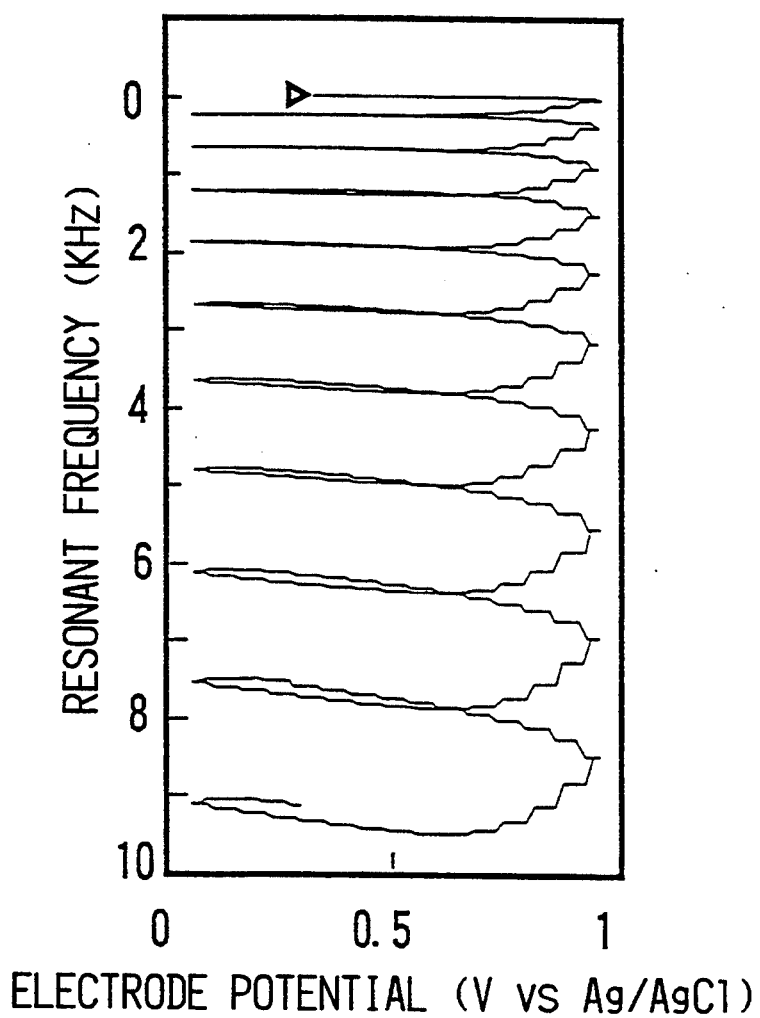
FIG. 3 is a graph showing an example of the resonant frequency vs. electrode potential curve measured in the same reaction as the FIG. 2 case.
Figure 4:
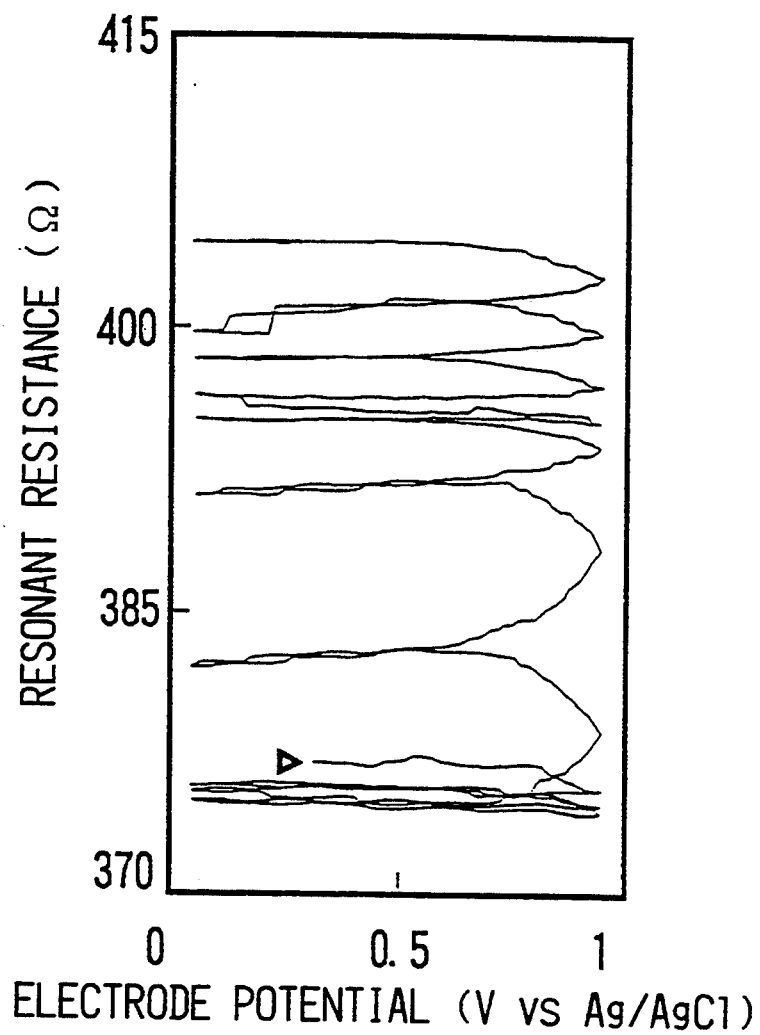
FIG. 4 is a graph showing an example of the resonant resistance vs. electrode potential curve measured in the same reaction as the FIG. 2 case.

The electrolytic polymerization of pyrrole was conducted by an electrode potential cyclic scan method (50 mV/sec). FIG. 2 shows the cell current variation relative to the electrode potential. FIG. 3 shows an oscillating frequency variation with respect to the electrode potential. FIG. 4 shows a resonant resistance variation which was calculated according to the measured value of the amplitude VQ, with respect to the electric potential. Before and after the reaction, the measured resonant frequency and the resonant resistance in terms of the measured amplitude well coincided with results obtained by the impedance analyzer.

Figure 5:
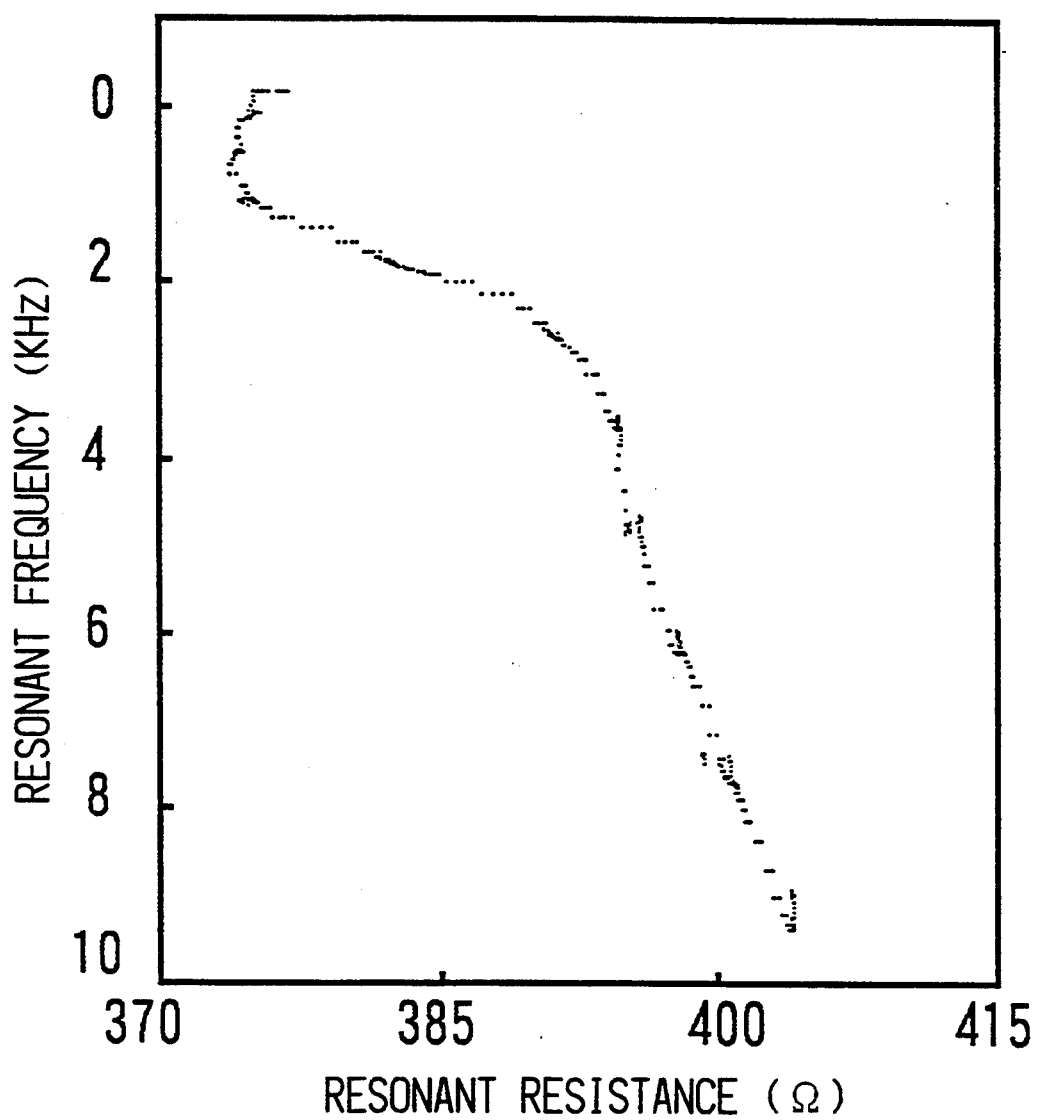
FIG. 5 is a graph showing the relation between the resonant resistance and the resonant frequency.

FIG. 5 shows the relation between the resonant frequency variation and the resonant resistance of the quartz crystal resonator. As understood from the FIG. 5 graph, in the initial stage of the polymerization, an elastic film was grown since the resonant resistance was not changed in contrast to the resonant frequency variation. When the polymerization progressed, it was observed that the film acquired the viscoelastic nature since the resistance increased.

In this analytic measurement, the formation of an electrolytically polymerized film may be conducted by other methods such as a constant-potential electrolytic method and a constant-current electrolytic method. Further, the inventive system can be applied to analysis of corrosion or passivation which occurs on the working electrode surface.

The inventive electrochemical measurement system is constructed such as to measure the resonant frequency and resonant resistance of the quartz crystal resonator concurrently with the monitoring of cell current and electrode potential during the course of the electrochemical reaction, thereby enabling analysis of the relation between mass variation and viscoelastic variation in the growth process of a film on the electrode.

Next, the description is given for another application of the FIG. 1 system which is directed to analysis of an electrochemical migration. In this measurement, a Pt wire electrode was used as the counter electrode 6, and a saturated calomel electrode was used as the reference electrode 5. The electrolyte solution was prepared in the form of 20 ml of 0.1M phosphoric acid buffer solution (pH 7). An AT cut type quartz crystal resonator having a frequency of 9 MHz was provided and its Pt electrode was provisionally coated with a macromolecule sensitive film. The resonator 1 was dipped into the electrolyte solution containing a certain density of an electrochemically active species. Prior to the measurement, it was confirmed that the resonant frequency and the resonant resistance were kept stable under room temperature. The precoated macromolecule film was comprised of a solid polymer electrolyte film composed of an ion exchange fluororesin which features high thermal resistance and good chemical stability. This ion exchange fluororesin has the following composition

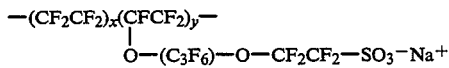

Figure 6:
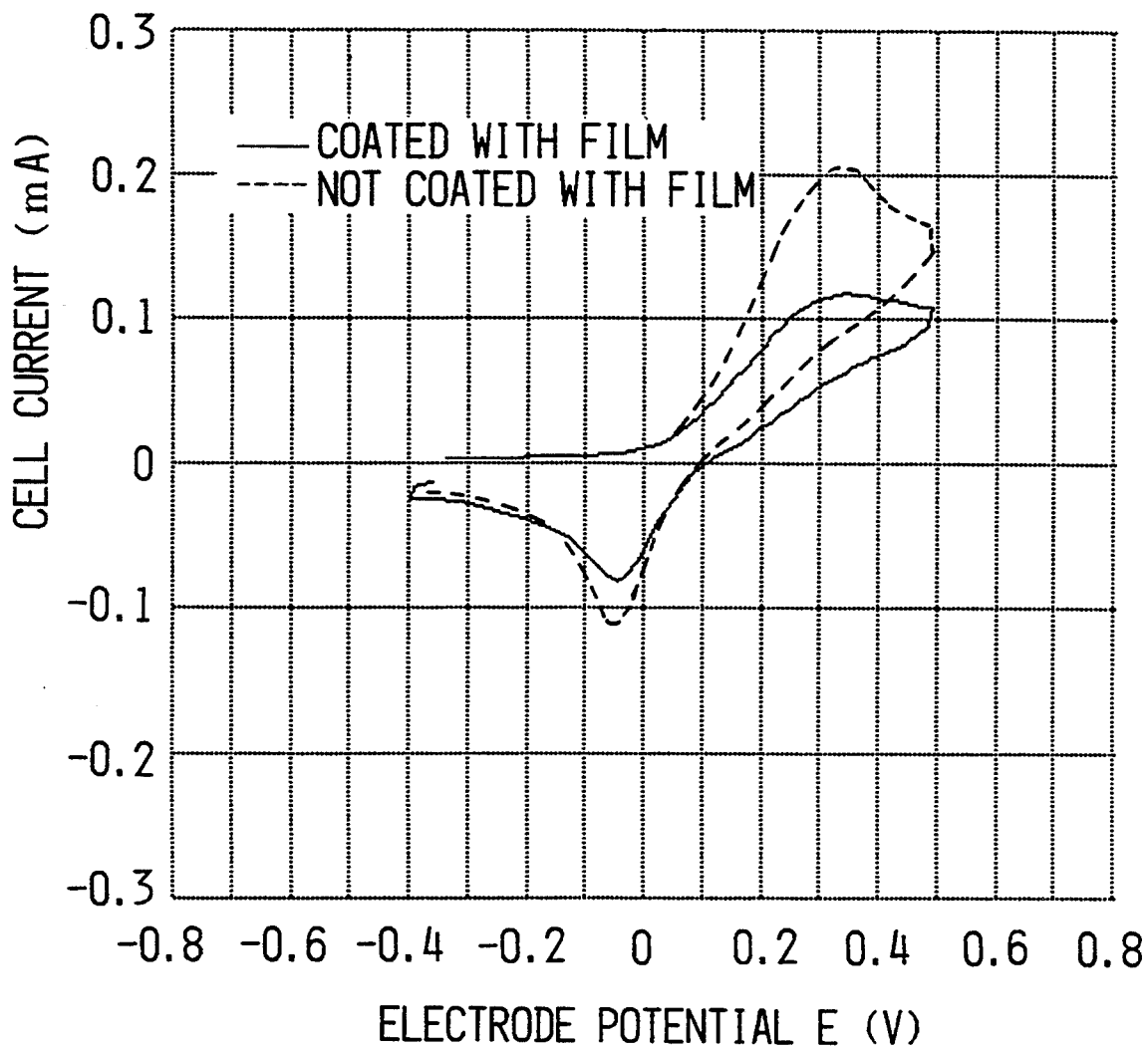
FIG. 6 is a graph showing the cell current vs. electrode potential curve measured by the inventive electrochemical measurement system when using hydroquinone as a sample species.
Figure 7:
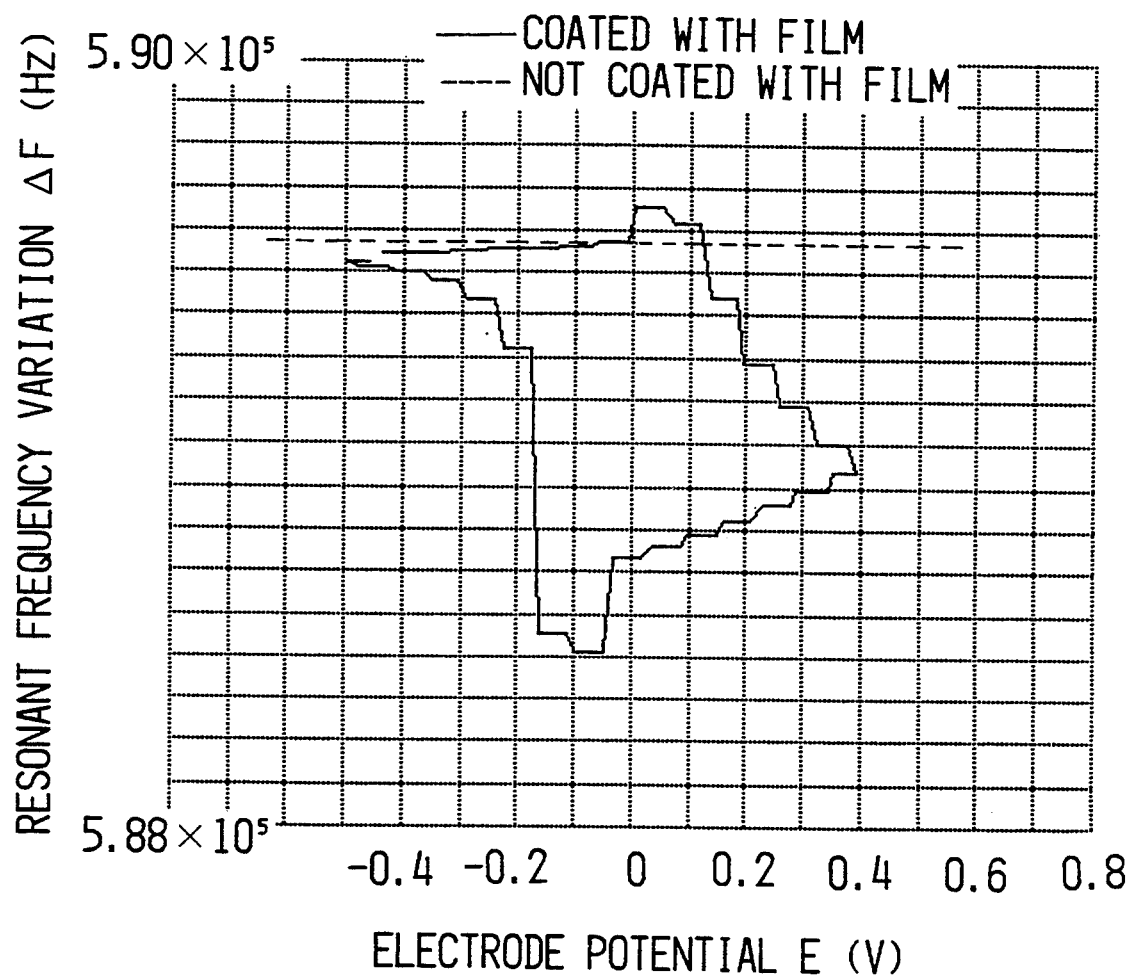
FIG. 7 is a graph showing the resonant frequency vs. electrode potential curve measured in the same condition as the FIG. 6 case.
Figure 8:
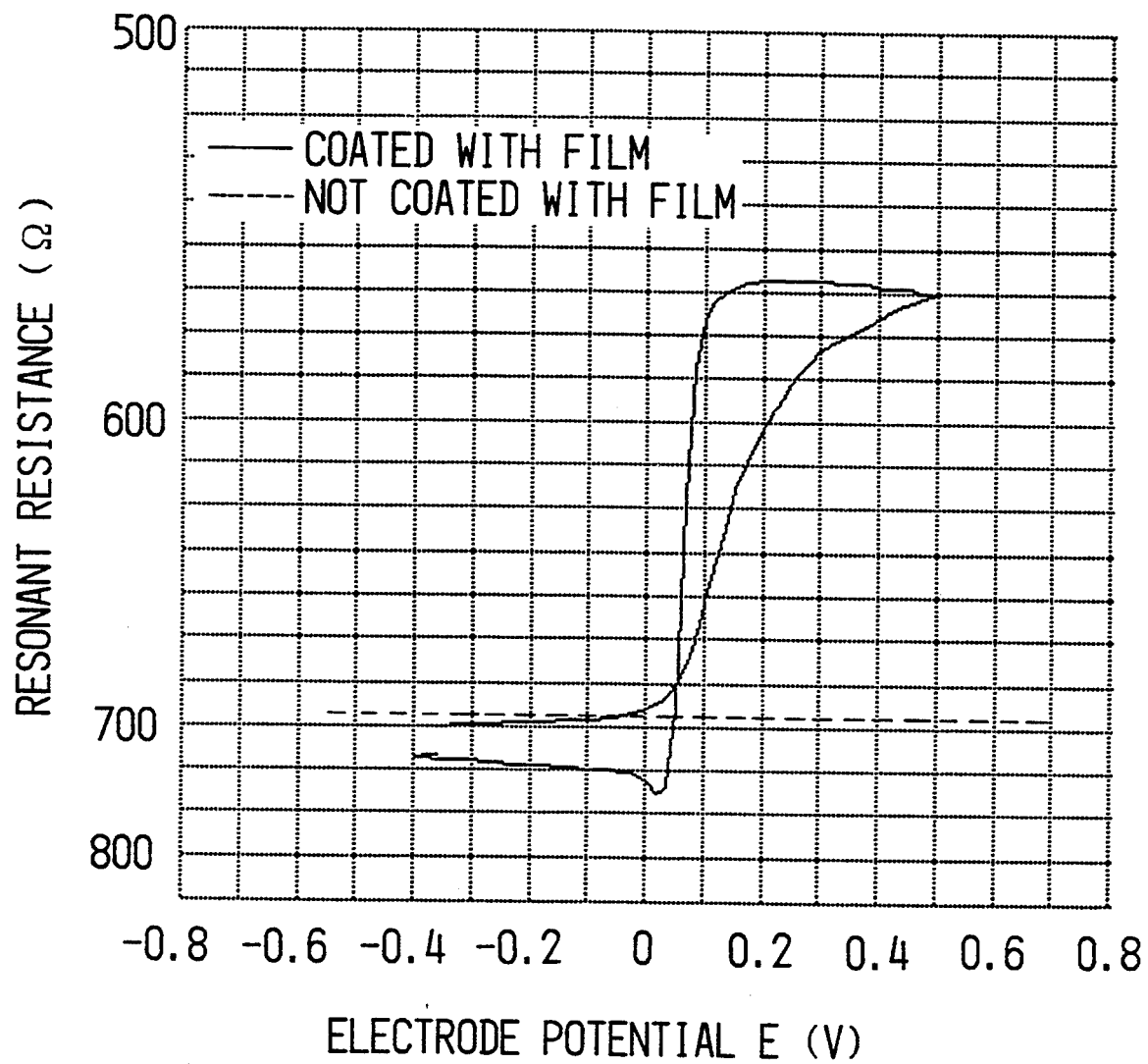
FIG. 8 is a graph showing the resonant resistance vs. electrode potential curve measured in the same condition as the FIG. 6 case.

FIG. 6 shows the current vs. potential curve or cyclic voltammetry which was measured by sweeping the electrode potential by the rate of 50 mV/s wherein hydroquinone phosphoric acid buffer soultion (3.5 mM) was tested as a typical electrochemically active species. FIG. 7 shows the resonant frequency vs. electrode potential curve, and FIG. 8 shows the resonant resistance vs. electrode potential curve measured in the same condition. For comparison purposes, the measurement was effected under the same condition using a quartz crystal resonator having an exposed Pt electrode which was not coated with the sensitive film, and the results of the measurement are also shown in these figures.

In the case of the exposed or noncoated Pt electrode, no variation was observed in the measured resonant frequency and resonant resistance while the cyclic voltammetry indicated some electrochemical behavior. On the other hand in the case of using the quartz crystal resonator having an electrode coated with the sensitive film, significant variation was observed in the resonant frequency characteristic and the resonant resistance characteristic in response to an oxidation peak or a reduction peak observed in the cyclic voltammetry. Such variation was caused by a decrease of initial hydroquinone density and an increase of resulting quinone density in the vicinity of the electrode. Such density variations would cause migration of the substances due to diffusion of hydroquinone and quinone to and from the sensitive film, and would cause viscous nature variation within the film due to interaction between the film material and the diffused substances. In the present invention, the macromolecule sensitive film can be selected generally from an ion exchange resin film, a solid polymer electrolyte film, an electroconductive macromolecule film and so on.

According to this application of the inventive electrochemical measurement system, the quartz crystal resonator precoated with a macromolecule film is utilized to monitor the electrochemical reaction in terms of both the resonant frequency and the resonant resistance, thereby enabling analysis of transformation and migration of substances and associated viscosity variation within the film coated over the electrode during the course of an electrochemical reaction.

What is claimed is:

1. A system for effecting analysis of an electrochemical reaction conducted within a cell having a working electrode, a counter electrode and a reference electrode disposed in an electrolyte solution, the system comprising:

an electrochemical measurement unit composed of a potentiostat connected to the working electrode, the counter electrode and the reference electrode for measuring a cell current flowing through the cell and an electrode potential of the working electrode;

a quartz crystal resonator having an electrode which functions as the working electrode;

a characteristic measurement unit comprising an oscillating circuit operative to apply a drive signal to the working electrode for oscillating the resonator, a first measurement circuit for measuring a resonant frequency variation of the resonator, and a second measurement circuit for measuring a resonant resistance variation of the resonator in terms of an amplitude level variation of the drive signal; and means for analyzing the electrochemical reaction based on concurrently measured results of the cell current, the electrode potential of the working electrode, the resonant frequency variation, and the resonant resistance variation.

2. A system according to claim 1; wherein the resonator comprises an AT cut quartz crystal resonator having one electrode disposed in contact with the electrolyte solution to function as the working electrode and another electrode electrically isolated from the electrolyte solution.

3. A system for effecting analysis of an electrochemical reaction conducted within a cell having a working electrode, a counter electrode and a reference electrode disposed in an electrolyte solution, the system comprising:

an electrochemical measurement unit comprising a potentiostat connected to the working electrode, the counter electrode and the reference electrode for measuring a cell current flowing through the cell and an electrode potential of the working electrode;

a quartz crystal resonator having an electrode which is precoated with a sensitive film and which functions as the working electrode;

a characteristic measurement unit comprising an oscillating circuit operative to apply a drive signal to the working electrode for oscillating the resonator, a first measurement circuit for measuring a resonant frequency variation of the resonator, and a second measurement circuit for measuring a resonant resistance variation of the resonator in terms of an amplitude level variation of the drive signal; and means for analyzing the electrochemical reaction on and in the sensitive film based on concurrently measured results of the cell current, the electrode potential of the working electrode, the resonant frequency variation, and the resonant resistance variation.

4. A system according to claim 3; wherein the resonator comprises an AT cut quartz crystal resonator having one electrode disposed in contact with the electrolyte solution to function as the working electrode and another electrode electrically isolated from the electrolyte solution.

5. A system according to claim 3; wherein the sensitive film is a macromolecule film selected from the group consisting of an ion exchange resin film, a solid polymer electrolyte film and an electroconductive macromolecule film.

6. A system for measuring and analyzing an electrochemical reaction, comprising:
   a cell within which an electrochemical reaction is conducted, the cell having a working electrode, a counter electrode and a reference electrode all disposed in an electrolyte solution contained in the cell during use of the system;
   an electrochemical measurement unit connected to each of the electrodes for measuring a cell current flowing through the cell and an electrode potential of the working electrode;
   resonating means operative when excited by a drive signal to undergo oscillation and having an electrode which functions as the working electrode for exciting the resonating means;
   an oscillating circuit for applying a drive signal having a varying characteristic to the working electrode to oscillate the resonating means;
   a first measurement circuit for measuring a resonant frequency variation of the resonating means;
   a second measurement circuit for measuring a resonant resistance variation of the resonating means in accordance with a variation of the varying characteristic of the drive signal; and
   means for analyzing the electrochemical reaction based on concurrently measured results of the cell current, the electrode potential of the working electrode, the resonant frequency variation and the resonant resistance variation.

7. A system according to claim 6; wherein the electrochemical measurement unit comprises a potentiostat.

8. A system according to claim 6; wherein the resonating means comprises a quartz crystal resonator.

9. A system according to claim 8; wherein the quartz crystal resonator has a first electrode disposed in contact with the electrolyte solution to function as the working electrode and a second electrode electrically isolated from the electrolyte solution.

10. A system according to claim 9; wherein the quartz crystal resonator has a resonant frequency of 9 MHz.

11. A system according to claim 6; wherein the first measurement circuit comprises a frequency counter.

12. A system according to claim 6; wherein the second measurement circuit comprises an amplitude level meter.

13. A system according to claim 6; wherein the means for analyzing the electrochemical reaction comprises a CPU.

14. A system according to claim 6; wherein the resonating means comprises a quartz crystal resonator pre-coated with a sensitive film.

15. A system according to claim 14; wherein the sensitive film is a macromolecule film selected from the group consisting of an ion exchange resin film, a solid polymer electrolyte film and an electroconductive macromolecule film.

16. A system according to claim 14; including means for analyzing the electrochemical reaction on and in the sensitive film based on concurrently measured results of the cell current, the electrode potential of the working electrode, the resonant frequency variation and the resonant resistance variation.

17. A system according to claim 6; wherein the varying characteristic of the drive signal comprises amplitude.

* * * * *